United States Patent [19]

Howe

[11] 4,229,204
[45] Oct. 21, 1980

[54] TRIFLUOROMETHYLPHENYL ISOXAZOLYL BENZOATES

[75] Inventor: Robert K. Howe, Bridgeton, Mo.

[73] Assignee: Monsanto Company, St. Louis, Mo.

[21] Appl. No.: 966,403

[22] Filed: Dec. 4, 1978

Related U.S. Application Data

[63] Continuation-in-part of Ser. No. 907,069, May 18, 1978, abandoned, which is a continuation-in-part of Ser. No. 796,248, May 12, 1977, abandoned.

[51] Int. Cl.² .................... C07D 261/08; H01N 9/28
[52] U.S. Cl. ............................................ 71/88; 71/74; 71/76; 548/247
[58] Field of Search .................. 260/307 H; 71/88

[56] References Cited

U.S. PATENT DOCUMENTS

| 3,772,284 | 11/1973 | Singh et al. ................ 260/307 H |
| 3,882,138 | 5/1975 | Brouwer et al. .................... 71/90 |
| 3,947,263 | 3/1976 | Brouwer et al. .................... 71/88 |
| 3,987,179 | 10/1976 | Nadelson ................... 260/307 H |
| 4,032,644 | 6/1977 | Nadelson ................... 260/307 H |
| 4,060,402 | 11/1977 | Tomlta et al. ................... 71/88 |
| 4,065,463 | 12/1977 | Beck et al. .................. 260/307 H |
| 4,112,108 | 9/1978 | Nadelson ................... 260/307 H |
| 4,129,568 | 12/1978 | Howe .................................. 71/88 |
| 4,140,515 | 2/1979 | Howe ........................ 260/307 H |

FOREIGN PATENT DOCUMENTS 837454  1/1975  Belgium ........................ 260/307 H

OTHER PUBLICATIONS

Katekar; Phytochemistry, vol. 15, pp. 1421–1424 (1976).

Primary Examiner—Mary C. Lee
Attorney, Agent, or Firm—Richard H. Shear; Donald W. Peterson

[57] ABSTRACT

The invention relates to 3-trifluoromethylphenylisoxazol-5-yl-benzoates and their use as herbicides or plant growth regulants.

23 Claims, No Drawings

TRIFLUOROMETHYLPHENYL ISOXAZOLYL BENZOATES

This application is a continuation-in-part of application Serial No. 907,069, filed May 18, 1978, which is a continuation-in-part of application Serial No. 796,248, filed May 12, 1977, both now abandoned.

This invention relates to 3-trifluoromethylphenylisoxazol-5-yl-benzoates as well as their use as agricultural chemicals. The novel compounds have been found to be effective in controlling the growth of undesired vegetation. At lower rates, the compounds have been found to be effective in regulating the growth of desirable plants.

The compounds of the invention may be represented by the following chemical formula

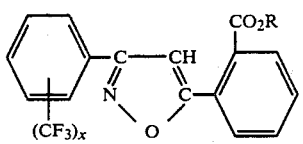

wherein x is one or two; and R is hydrogen, lower alkyl or agriculturally acceptable cations.

The isoxazol-5-yl-benzoates of the invention may be prepared by reacting the appropriate hydroxamoyl chloride with an o-vinylbenzoate under basic conditions (such as in the presence of tertiary amines) to form the isoxazolin-5-yl-benzoate which can then be converted to the isoxazol-5-yl-benzoate either upon heating with N-bromosuccinimide or dichlorodicyanobenzoquinone. In order to clarify the above, the following reaction scheme is presented:

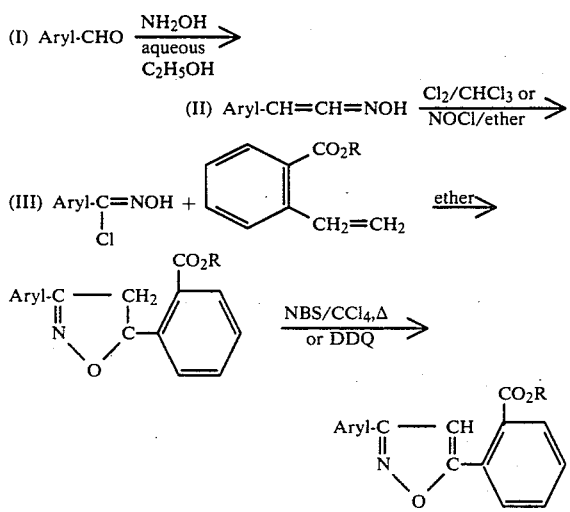

As is apparent to those skilled in the art, the appropriate hydroxamoyl chloride is prepared in accordance with the above reaction scheme by reaction of hydroxylamine with an aryl aldehyde in aqueous alcohol to form Compound II which can then be chlorinated to the hydroxamoyl chloride (III).

Aryl aldehydes may be prepared by the procedure of Jolad and Rajagopal, *Org. Syn. Coll.*, Vol. V, Page 139 (1973). The o-vinylbenzoate may be prepared by treatment of vinylbenzoic acid with thionyl chloride and then with an alcohol. o-Vinylbenzoic acid may be prepared in accordance with the following examples which are presented as an illustration of the above procedure.

EXAMPLE 1

Preparation of o-Vinylbenzoic Acid

The sodium salt of 2-carboxybenzaldehyde was prepared by addition of 129.6 g (0.60 mol) of 25% sodium methoxide in methanol to a solution of 90 g (0.6 mol) of 2-carboxybenzaldehyde in 900 ml. of methanol, followed by concentration under vacuum to 90° C. at 0.5 torr.

Methylenetriphenylphosphorane was prepared on a 0.605 mol scale in dimethylsulfoxide from methyltriphenylphosphonium bromide and dimsylsodium as described in E. J. Corey et al, *J. Org. Chem.*, Vol. 28, Page 1128 (1963). Then the sodium carboxylate was added with stirring under $N_2$. After a few minutes, the solution was concentrated under oil pump vacuum (45° C. maximum bath temperature), and water was added to the residue. The mixture was filtered, and to the filtrate was added 57 ml. of concentrated HCl with stirring. The resultant mixture was extracted with ether. The ether solution was extracted with 5% NaOH. The aqueous layer was acidified with HCl and then extracted with ether. The ether solution was dried and concentrated under vacuum to 61 g (69%) of sticky solid. A small portion was recrystallized from pet ether to give 1.5 g of solid, mp 89°–90° C.

EXAMPLE 2

Preparation of Methyl o-Vinylbenzoate

A mixture of 58.5 g (0.395 mol) of o-vinylbenzoic acid and 127.3 g (1.08 mol) of thionyl chloride was heated on a steam bath (strong gas evolution) for 40 minutes until gas evolution subsided. The solution was concentrated, and 270 ml. of methanol was added slowly. The mixture was held at reflux for 10 minutes and then was concentrated. Ether was added to the residue, and the solution was extracted three times with water. The ether layer was dried, a little hydroquinone was added, and the solution was distilled to give 32.2 g (50.5%) of liquid, B.P. 64°–78° C. (0.2 torr).

EXAMPLE 3

Preparation of Methyl 2-[3-[3-(Trifluoromethyl)-Phenyl]-5-Isoxazolyl]Benzoate

A solution of 8.67 g (0.0858 mol) of triethylamine in 25 ml. of ether was added dropwise with stirring to a solution of 19.19 g (0.0858 mol) of m-trifluoromethylbenzohydroxamoyl chloride and 13.9 g (0.0858 mol) of methyl o-vinylbenzoate in 200 ml. of ether at 0°–5° C. during 45 minutes. The mixture was stirred in an ice bath for 2 hours and then at 20° C. for 21 hours, and then was washed three times with water. The ether layer was filtered to remove a little gelatinous solid, and the filtrate was dried ($CaSO_4$) and concentrated under vacuum to 10 torr at 60° C. to give 29.5 g (98%) of oil, methyl 2-[3-[3-(trifluoromethyl)phenyl]-2-isoxazolin-5-yl]benzoate.

A solution of 26.74 g (0.0766 mol) of the isoxazoline from above and 13.6 g (0.0766 mol) of N-bromosuccinimide in 250 ml. of $CCl_4$ was heated with stirring at reflux. A 0.5 g sample of benzoyl peroxide was added; after 10–15 minutes the red color of $Br_2$ was evident. After the reaction mixture was held at reflux for 1 hour, another 0.1 g of benzoyl peroxide was added, and heating was continued for another hour. The reaction mixture was allowed to cool and was filtered free of succinimide. The filtrate was concentrated under vacuum, and the residual oil was subjected to Kugelrohr distillation at 140°–170° C. (0.2 torr); a temporary loss of vacuum to 1–2 mm occurred when the pot temperature reached 140° C., and a sour smell emitted from the oil pump, indicative of HBr evolution. The distillate was subjected to another Kugelrohr distillation to give 20.01 g of 98% pure product as a viscous oil. Crystallization of the oil from ether-hexane at 0° C. gave 13.86 g of solid, mp 46.5°–48.5° C.

Anal. Calc'd. for $C_{18}H_{12}F_3NO_3$: C, 62.25; H, 3.48; N, 4.03. Found: C, 62.33; H, 3.49; N, 4.09.

Similarly, the following compounds may be prepared.

| Example No. | Compound |
| --- | --- |
| 4 | Ethyl 2-[3-[3-(Trifluoromethyl)Phenyl]-5-Isoxazolyl]Benzoate. |
| 5 | n-Propyl 2-[3-[3-(Trifluoromethyl)Phenyl]-5-Ixoxazolyl]Benzoate. |
| 6 | n-Butyl 2-[3-[3-(Trifluoromethyl)Phenyl]-5-Isoxazolyl]Benzoate. |
| 7 | n-Pentyl 2-[3-[3-(Trifluoromethyl)Phenyl]-5-Isoxazolyl]Benzoate. |
| 8 | Isopropyl 2-[3-[3-(Trifluoromethyl)Phenyl]-5-Isoxazolyl]Benzoate. |
| 9 | sec-Butyl 2-[3-[3-(Trifluoromethyl)Phenyl]-5-Isoxazolyl]Benzoate. |
| 10 | tert-Butyl 2-[3-[3-(Trifluoromethyl)Phenyl]-5-Isoxazolyl]Benzoate. |

Acids may be prepared by hydrolysis of the appropriate ester. Salts may be prepared by reaction of the appropriate base with the free acid.

EXAMPLE 4

Preparation of 2-[3-(3-Trifluoromethylphenyl)-5-Isoxazolyl]Benzoic Acid

A solution of 6.20 g of methyl 2-[3-(3-trifluoromethylphenyl)-5-isoxazolyl]benzoate, 75 ml. of acetic acid, and 50 ml. of concentrated HCl was held at reflux for 4 hours, cooled, and poured into 450 ml. of cold water. The resultant solid was recrystallized from $CH_3CN$ to give 3.87 g of solid, mp 176°–177° C.

Anal. Calc'd. for $C_{17}H_{10}F_3NO_3$: C, 61.27; H, 3.02. Found: C, 61.25; H, 3.03.

As used herein, the term "lower alkyl" is understood to mean those alkyl groups having from 1 to 5 carbon atoms, inclusive, including straight and branched chains.

The term "agriculturally acceptable cations" is understood to mean those cations which are commonly used in agricultural compositions to form the salt of the free acid, including but not limited to the alkali metal, substituted amine and ammonium cations such as isopropylamine, triethanolamine, etc.

As noted above, the compounds of the present invention have been found to be effective in the partial or total inhibition of undesirable vegetation. Tables I and II summarize results of tests conducted to determine the pre-emergent as well as the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species which were pressed into the soil surface. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 4 weeks after seeding and treating, the plants were observed and the results recorded. Tables I and II below summarize such results. The herbicidal rating was obtained by means of a fixed scale based on the percent injury of each plant species. The ratings are defined as follows:

| % Control | Rating |
| --- | --- |
| 0–24 | 0 |
| 25–49 | 1 |
| 50–74 | 2 |
| 75–100 | 3 |

The post-emergent tests were conducted as follows:

The active ingredients are applied in spray form to two or three week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects ranging from partial to total inhibition are observed and recorded. The results are shown in Table I in which the post-emergent herbicidal activity index is as follows:

| % Control | Rating |
| --- | --- |
| 0–24 | 0 |
| 25–49 | 1 |
| 50–74 | 2 |
| 75–99 | 3 |
| 100 | 4 |

The plant species utilized in these tests are identified by letter in accordance with the following legend:

| | |
| --- | --- |
| A-Soybean | I-Hemp Sesbania |
| B-Sugarbeet | J-Lambsquarters |
| C-Wheat | K-Smartweed |
| D-Rice | L-Velvetleaf |
| E-Sorghum | M-Downy Brome |
| F-Cocklebur | N-Panicum Spp. |
| G-Wild Buckwheat | O-Barnyardgrass |
| H-Morningglory | P-Crabgrass |

Table I

| Compound of Example No. | WAT* | kg/h | Pre-Emergent Plant Species | | | | | | | | | | | | | | | |
| --- | --- | --- | --- | --- | --- | --- | --- | --- | --- | --- | --- | --- | --- | --- | --- | --- | --- | --- |
| | | | A | B | C | D | E | F | G | H | I | J | K | L | M | N | O | P |
| 3 | - | 4 | 1.12 | 2 | 2 | 1 | 3 | 2 | 1 | 2 | 2 | 3 | 1 | 3 | 1 | 1 | 2 | 3 | 2 |

Table I-continued

| | | | A | B | C | D | E | F | G | H | I | J | K | L | M | N | O | P |
|---|---|---|---|---|---|---|---|---|---|---|---|---|---|---|---|---|---|---|
| 3 | 4 | 5.60 | 3 | 3 | 2 | 3 | 3 | 2 | 3 | 3 | 3 | 2 | 3 | 2 | 2 | 3 | 3 | 2 |
| 4 | 4 | 1.12 | 1 | 1 | 0 | 3 | 2 | 0 | 2 | 2 | 1 | 3 | 3 | 0 | 1 | 2 | 3 | 1 |
| 4 | 4 | 5.60 | 3 | 2 | 1 | 3 | 3 | 1 | 2 | 3 | 2 | 2 | 3 | 1 | 2 | 3 | 3 | 3 |
| 6 | 2 | 0.28 | 0 | 1 | 0 | 2 | 0 | 0 | 3 | 1 | 1 | 3 | 3 | 0 | 2 | 3 | 3 | 3 |
| 6 | 2 | 1.12 | 1 | 2 | 1 | 3 | 1 | 0 | 2 | 1 | 3 | 3 | 3 | 0 | 1 | 1 | 3 | 2 |
| 6 | 2 | 5.60 | 3 | 2 | 1 | 3 | 3 | 1 | 3 | 3 | 2 | 3 | 3 | 2 | 3 | 2 | 3 | 3 |
| 7 | 4 | 0.28 | 0 | 3 | 0 | 1 | 0 | 0 | 3 | 0 | 0 | 1 | 0 | 0 | 2 | — | 2 | 0 |
| 7 | 4 | 1.12 | 0 | 2 | 1 | 2 | 1 | 0 | 2 | 2 | 1 | 2 | 2 | 0 | 1 | 0 | 2 | 0 |
| 7 | 4 | 5.60 | 3 | 2 | 1 | 3 | 3 | 1 | 2 | 2 | 2 | 2 | 2 | 1 | 2 | 2 | 3 | 3 |
| 11 | 4 | 1.12 | 3 | 2 | 0 | 3 | 1 | 0 | 2 | 1 | 3 | 2 | 2 | 1 | 2 | 2 | 3 | 2 |
| 11 | 4 | 5.60 | 3 | 2 | 1 | 3 | 3 | 1 | 3 | 2 | 2 | 3 | 3 | 2 | 2 | 3 | 2 | 3 |

| | | | Post-Emergent Plant Species | | | | | | | | | | | | | | | |
|---|---|---|---|---|---|---|---|---|---|---|---|---|---|---|---|---|---|---|
| Compound of Example No. | WAT* | kg/h | A | B | C | D | E | F | G | H | I | J | K | L | M | N | O | P |
| 3 | 2 | 1.12 | 1 | 0 | 1 | 0 | 0 | 1 | 1 | 1 | 1 | 1 | 1 | 1 | 0 | 0 | 0 | 0 |
| 3 | 4 | 5.60 | 1 | 1 | 0 | 0 | 0 | 1 | 1 | 1 | 0 | 1 | 1 | 1 | 0 | 0 | 0 | 0 |
| 4 | 4 | 1.12 | 2 | 1 | 0 | 1 | 1 | 2 | 2 | 2 | 2 | 1 | 2 | 2 | 0 | 0 | 2 | 1 |
| 4 | 4 | 5.60 | 2 | 2 | 1 | 1 | 2 | 2 | 2 | 2 | 2 | 2 | 4 | 1 | 0 | 1 | 3 | 2 |

*Weeks after treatment.

The compounds were also tested by utilizing the above procedure on the following plant species:

| | |
|---|---|
| A-Canada Thistle | G-Yellow Nutsedge |
| B-Cocklebur | H-Quackgrass |
| C-Velvetleaf | I-Johnsongrass |
| D-Morningglory | J-Downy Brome |
| E-Lambsquarters | K-Barnyardgrass |
| E-Smartweed | |

The results are summarized by Table II.

Table II

| | | | Pre-Emergent Plant Species | | | | | | | | | | |
|---|---|---|---|---|---|---|---|---|---|---|---|---|---|
| Compound of Example No. | WAT* | kg/h | A | B | C | D | E | F | G | H | I | J | K |
| 3 | 2 | 11.2 | 3 | 2 | 2 | 2 | 3 | 3 | 2 | 3 | 2 | 2 | 3 |
| 4 | 4 | 11.2 | 2 | 1 | 2 | 2 | 2 | 2 | 0 | 2 | 0 | 2 | 3 |
| 6 | 4 | 11.2 | 3 | 1 | 1 | 3 | 2 | 3 | 1 | 2 | 0 | 3 | 3 |
| 7 | 4 | 11.2 | 1 | 1 | 0 | 1 | 3 | 2 | 0 | 2 | 1 | 1 | 3 |
| 8 | 2 | 11.2 | 0 | 0 | 0 | 0 | 3 | 0 | 0 | 1 | 0 | 0 | 0 |
| 11 | 4 | 11.2 | 3 | 3 | 3 | 2 | 2 | 3 | 1 | 3 | 0 | 3 | 3 |

| | | | Post-Emergent Plant Species | | | | | | | | | | |
|---|---|---|---|---|---|---|---|---|---|---|---|---|---|
| Compound of Example No. | WAT* | kg/h | A | B | C | D | E | F | G | H | I | J | K |
| 3 | 4 | 11.2 | 2 | 2 | 2 | 2 | 4 | 4 | 0 | 3 | 2 | 2 | 3 |
| 4 | 4 | 11.2 | 2 | 1 | 2 | 2 | 3 | 2 | 1 | 1 | 1 | 0 | 3 |
| 6 | 4 | 11.2 | 2 | 1 | 1 | 2 | 1 | 2 | 0 | 1 | 1 | 0 | 2 |
| 7 | 4 | 11.2 | 2 | 2 | 1 | 2 | 1 | 1 | 1 | 0 | 2 | 0 | 1 |
| 8 | 4 | 11.2 | 0 | 1 | 0 | 2 | 2 | 1 | 0 | 0 | 0 | 0 | 1 |
| 11 | 4 | 11.2 | 1 | 1 | 1 | 1 | 2 | 2 | 1 | 0 | 1 | 2 | 2 |

*Weeks after treatment.

The above table illustrates one aspect of the present invention. That is, the use of the compounds of the invention to kill or injure undesirable plants, e.g., weeds. The compounds are especially effective when applied as a pre-emergent and have been found to be selective toward wheat. Another aspect of the invention, however, is the use of said compounds for the regulation of desirable plant growth especially dicotyledonous plants such as legumes, trees and sugarbeets.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth, it does not include the total inhibition of killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

Utilizing the isoxazol-5-yl-benzoates as the active ingredient in a plant growth regulating composition, said compounds were found to possess plant growth regulating activity when tested in accordance with the following procedure.

Soybean plants, variety Clark 63, were grown in a greenhouse or a growth chamber to the one-half expanded unifoliate stage. At that time, the plants were treated by dipping the plants into an aqueous solution of the chemical, acetone and a surfactant. After growing the plants for approximately two weeks under cool conditions (11°–14° C.), the plants were transferred to a greenhouse and grown at 24° C. Approximately four weeks after treatment, the plants were observed and compared with control plants that had been dipped into water containing only the surfactant. Results are summarized by Table III.

Table III

| Compound of Example No. | Chemical Concentration (ppm) | Observations |
|---|---|---|
| 3 | 133 | Stature reduction, axillary bud development. |
| 3 | 400 | Stature reduction, axillary bud development. |
| 4 | 266 | Stature reduction, axillary bud development, reduced leaf size, darker green leaves. |
| 6 | 266 | Stature reduction, axillary bud development, reduced leaf size, leaf curl, darker green leaves. |
| 7 | 266 | Stature reduction, axillary bud development, reduced leaf size, leaf curl, darker green leaves. |
| 11 | 266 | Stature reduction, axillary bud development, darker green leaves, inhibition of apical development. |

The compounds of Example Numbers 3, 4, 6 and 7 were further tested as follows.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Results are summarized in Table IV, below.

Table IV

| Compound of Example No. | Rate (kg/h) | Observations |
|---|---|---|
| 3 | 0.112 | Stature reduction, leaf alteration, rosette growth, altered canopy, inhibition of apical development, inhibition of dry weight. |
| 3 | 0.56 | Stature reduction, leaf alteration, rosette growth, altered canopy, inhibition of apical development, inhibition of dry weight. |
| 3 | 2.8 | Stature reduction, leaf alteration, rosette growth, altered canopy, inhibition of apical development, inhibition of dry weight, slighty phytotoxicity. |
| 4 | 0.112 | Stature reduction, leaf distortion of new growth, leaf alteration, dark foliar color, inhibition of apical development, inhibition of dry weight. |
| 4 | 0.56 | Stature reduction, leaf distortion of new growth, leaf alteration, dark foliar color, inhibition of apical development, inhibition of dry weight. |
| 4 | 2.8 | Stature reduction, leaf distortion of new growth, leaf alteration, dark foliar color, inhibition of apical development, inhibition of dry weight. |
| 6 | 0.112 | Stature reduction, leaf alteration of new growth, leaf inhibition, thickening of leaf texture, dark foliar color, inhibition of dry weight |
| 6 | 0.56 | Stature reduction, leaf alteration of new growth, leaf inhibition, thickening of leaf texture, dark foliar color, inhibition of dry weight |
| 6 | 2.28 | Stature reduction, leaf alteration of new growth, leaf inhibition, thickening of leaf texture, dark foliar color, inhibition of dry weight |
| 7 | 0.112 | Stature reduction, leaf alteration of old and new growth, dark foliar color, inhibition of apical development, inhibition of dry weight. |
| 7 | 0.56 | Stature reduction, leaf alteration of old and new growth, dark foliar color, inhibition of apical development, inhibition of dry weight. |
| 7 | 2.28 | Stature reduction, leaf alteration of old and new growth, dark foliar color, inhibition of apical development, inhibition of dry weight. |

Additionally, the compound of Example Number 3 was tested as follows.

Williams soybeans were planted on 5.5 inch row spacings. The soybeans were treated at three different stages of early growth (first, second or third trifoliate opening) with a formulation of the compound of Example Number 3 containing 0.25% Tween 20 as a surfactant. Results are summarized in Table V, below.

Table V

| Rate of Application (lb/acre) | Stage of Application | Seed Yield (bu/acre) |
|---|---|---|
| — | — | 63.9 |
| 0.0125 | 1 | 67.4 |
| 0.0250 | 1 | 62.5 |
| 0.0375 | 1 | 59.6 |
| 0.0125 | 2 | 68.2 |
| 0.0250 | 2 | 64.7 |
| 0.0375 | 2 | 57.5 |
| 0.0125 | 3 | 65.7 |
| 0.0250 | 3 | 69.9 |
| 0.0375 | 3 | 70.3 |
| 0.0500 | 2 | 71.3 |
| 0.0062 | 2 | 63.6 |

The above data illustrates that yield increases may be effected by application of small amounts (0.0125 to 0.05 pounds per acre) of the compounds of the present invention.

The compound of Example Number 3 was also treated on various species of trees. Seedlings of said trees were potted and placed in the greenhouse after they had been subjected to a cold temperature environment (4° C.) for a period of approximately two months. When the buds broke and new growth appeared, the trunk and foliage were treated with an aqueous solution of the compound of Example Number 3, acetone, cyclohexanone and an emulsifier. Table VI summarizes the observations noted.

Table VI

| Tree Species | Rate mg/plant | Observation Period (Days) After Treatment) | Observations |
| --- | --- | --- | --- |
| Black Locust | 50 | 7-29 | Stature reduction, leaf epinasty, leaf inhibition, inhibition of branch growth. |
| Northern Red Oak | 20 | 28 | Stature reduction, leaf epinasty, stimulation of axillary buds, leaf inhibition, inhibition of apical development. |
| American Sycamore | 8 | 70 | Stature reduction, leaf epinasty, stimulation of axillary buds, leaf alteration, leaf inhibition, inhibition of apical development, inhibition of branch growth, enlarged nodes, increased number of branches at the node. |
| | 4 | 70 | Stature reduction, leaf epinasty, stimulation of axillary buds, leaf alteration, leaf inhibition, inhibition of apical development, inhibition of branch growth, enlarged nodes, increased number of branches at the node. |
| American Sycamore | 2 | 70 | Stature reduction, leaf epinasty, stimulation of axillary buds, leaf alteration leaf inhibition, inhibition of apical development, inhibition of branch growth, enlarged nodes, increased number of branches at the node. |

The compound of Example Number 3 was formulated as an aqueous solution of acetone, cyclohexanone and an emulsifier. Sugarbeet plants at the 5 to 7 leaf stage were treated with said formulation by wetting the leaves thereof. Table VII summarizes the results of observations taken 28 to 126 days after treatment.

Table VII

| Rate (ppm) | Observations |
| --- | --- |
| 10 | Stature reduction, leaf |

Table VII-continued

| Rate (ppm) | Observations |
| --- | --- |
| | inhibition, axillary bud development. |
| 100 | Stature reduction, leaf inhibition, reduced beet size, axillary bud development. |

The compounds of the invention have been found to be effective in regulating the growth of various monocotyledonous plants as well as dicotyledonous. The compound of Example Number 3 was tested on various lawn grasses as follows. A mixture of Kentucky Bluegrass, Creeping Red Fescue and Chewings Fescue were planted in a good grade of top soil in plastic pots. Seven to ten days after germination, the plants were treated with the active ingredient to which a surfactant had been added by spraying the plants until they were wet with various concentrations. Results are summarized in Table VIII.

Table VIII

| | Height (% of Control) at- | |
| --- | --- | --- |
| Rate (ppm) | 3 Weeks After Treatment | 9 Weeks After Treatment |
| 10 | 102 | 93 |
| 50 | 94 | 86 |
| 250 | 66 | 57 |

The compound of Example Number 3 was applied to four-week old Bluebell rice at a rate of 250 ppm. When compared with the control, stature reduction and tillering were noted both at 3 weeks and 7 weeks after treatment.

The compound of Example Number 3 was also applied to four-week old grain sorghum at a rate of 250 ppm. Results are summarized in Table IX.

Table IX

| Weeks After Treatment | Plant Height (% of Control) | Other Observations |
| --- | --- | --- |
| 3 | 91 | Chlorosis necrosis. |
| 7 | 81 | Necrosis. |

Table X, below, summarizes observations made when the compound of Example Number 3 was applied to harber barley.

Table X

| Time of Treatment | Time of Observation (Weeks after Treatment) | Concentration (ppm) | Plant Height (% of Control) |
| --- | --- | --- | --- |
| 16 days | 3 | 250 | 90 |
| 16 days | 6 | 250 | 97 |
| 42 days | 3 | 10 | 93 |
| 42 days | 3 | 50 | 106 |
| 42 days | 3 | 250 | 90 |

Table XI summarizes observations made when the compound of Example Number 3 was applied to cheyenne wheat.

Table XI

| Time of Treatment | Time of Observation (Weeks after Treatment) | Concentration (ppm) | Plant Height (% of Control) |
|---|---|---|---|
| 15 days | 3 | 250 | 80 |
| 15 days | 6 | 250 | 93 |
| 42 days | 3 | 10 | 113 |
| 42 days | 3 | 50 | 112 |
| 42 days | 3 | 250 | 109 |

Application of the compound of Example Number 4 to corn at 1330 ppm by dipping resulted in a reduction in stature and "buggy whipping" of the leaves.

The above data illustrate that the compounds of the invention may be used as a herbicide or a plant growth regulant for regulation of monocotyledonous or dicotyledonous plants. When used as a herbicide, it is desirable that rates of application above 2.24 kilograms per hectare be utilized although herbicidal activity at rates well below, e.g., 0.28 kilograms per hectare, have been found to be effective. When used to regulate the growth of desirable plants, rates below 5.6 kilograms per hectare especially 0.005 to 3.36 are preferred. Preferred are those compounds in which x is 1 and the $CF_3$ is in the meta position. Most preferred is the compound of Example Number 3, which is methyl 2-[3-[3-(trifluoromethyl)phenyl]-5-isoxazolyl]benzoate.

In selecting the appropriate time and rate of application of the active ingredient, it will be recognized that precise rates will also be dependent upon the desired response, mode of application, plant variety, soil conditions and various other factors known to those skilled in the art. While a rate of about 0.005 to 5.6 kilos per hectare is preferred, higher rates of up to 56 kilos per hectare may be used, depending upon the factors noted above. In addition, it will be recognized that single or multiple applications may be used to exert the desired response.

In the practice of the invention, the active ingredient can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

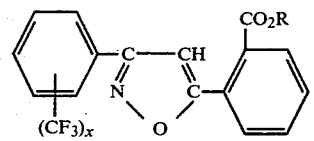

wherein x is 1 or 2; and R is hydrogen, lower alkyl or agriculturally acceptable cations.

2. A compound according to claim 1 wherein x is 1.

3. A compound according to claim 2 wherein the $CF_3$ is in the meta position.

4. A compound according to claim 3 wherein R is lower alkyl.

5. A compound according to claim 1 which is methyl 2-[3-[3-(trifluoromethyl)phenyl]-5-isoxazolyl]benzoate.

6. A compound according to claim 1 which is n-butyl 2-[3-[3-(trifluoromethyl)phenyl]-5-isoxazolyl]benzoate.

7. A method for preventing the growth of undesirable vegetation which comprises applying to said vegetation or the locus thereof a herbicidally effective amount of a compound having the formula

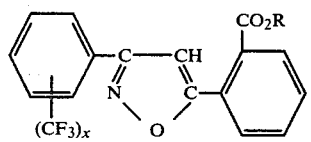

wherein x is 1 or 2; and R is hydrogen, lower alkyl or agriculturally acceptable cations.

8. A method according to claim 7 wherein x is 1.

9. A method according to claim 8 wherein the $CF_3$ is in the meta position.

10. A method according to claim 9 wherein R is lower alkyl.

11. A method according to claim 7 wherein said compound is methyl 2-[3-[3-(trifluoromethyl)phenyl]-5-isoxazolyl]benzoate.

12. A method according to claim 7 wherein said compound is n-butyl 2-[3-[3-(trifluoromethyl)phenyl]-5-isoxazolyl]benzoate.

13. A method of regulating the growth of desirable plants which comprises applying to said plants an effective amount of a compound having the formula

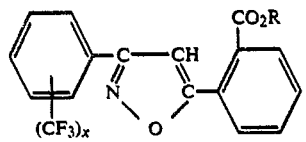

wherein x is 1 or 2; and R is hydrogen, lower alkyl or agriculturally acceptable cations.

14. A method according to claim 13 wherein x is 1.

15. A method according to claim 14 wherein the $CF_3$ is in the meta position.

16. A method according to claim 15 wherein R is lower alkyl.

17. A method according to claim 13 wherein said compound is methyl 2-[3-[3-(trifluoromethyl)phenyl]-5-isoxazolyl]benzoate.

18. An agricultural chemical composition comprising from about 1 to about 99 parts by weight of a compound having the formula

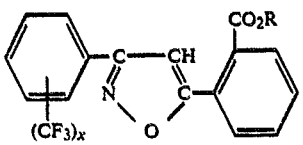

wherein x is 1 or 2; and R is hydrogen, lower alkyl or agriculturally acceptable cations; the remaining parts being comprised of one or more suitable adjuvants, carriers and/or diluents.

19. A composition according to claim 18 wherein x is 1.

20. A composition according to claim 19 wherein the $CF_3$ is in the meta position.

21. A composition according to claim 20 wherein R is lower alkyl.

22. A composition according to claim 18 wherein said compound is methyl 2-[3-[3-(trifluoromethyl)phenyl]-5-isoxazolyl]benzoate.

23. A composition according to claim 18 wherein said compound is n-butyl 2-[3-[3-(trifluoromethyl)phenyl]-5-isoxazolyl]benzoate.

* * * * *